(12) United States Patent
Kushida et al.

(10) Patent No.: US 7,501,431 B2
(45) Date of Patent: Mar. 10, 2009

(54) PHYSIOLOGICALLY ACTIVE SUBSTANCES PF1270A, B AND C SUBSTANCES

(75) Inventors: Nobuaki Kushida, Yokohama (JP); Naoko Watanabe, Yokohama (JP); Takashi Yaguchi, Odawara (JP); Fumikazu Yokoyama, Yokohama (JP); Goh Tsujiuchi, Odawara (JP); Takako Okuda, Yokohama (JP)

(73) Assignee: Meui Seika Kaisha, Ltd., Tokyo (JP)

( * ) Notice: Subject to any disclaimer, the term of this patent is extended or adjusted under 35 U.S.C. 154(b) by 484 days.

(21) Appl. No.: 10/551,417

(22) PCT Filed: Mar. 29, 2004

(86) PCT No.: PCT/JP2004/004416

§ 371 (c)(1),
(2), (4) Date: Sep. 30, 2005

(87) PCT Pub. No.: WO2004/087938

PCT Pub. Date: Oct. 14, 2004

(65) Prior Publication Data

US 2007/0105883 A1    May 10, 2007

(30) Foreign Application Priority Data

Mar. 31, 2003   (JP) .............................. 2003-093595

(51) Int. Cl.
A61K 31/4375 (2006.01)
C07D 471/20 (2006.01)
(52) U.S. Cl. ........................................ 514/278; 546/15
(58) Field of Classification Search .................. 514/278; 546/15
See application file for complete search history.

(56) References Cited

U.S. PATENT DOCUMENTS 3,817,835 A * 6/1974 Neidleman .................. 435/41
4,866,060 A * 9/1989 Mrozik ....................... 514/250
5,321,039 A   6/1994 Schwartz et al.

FOREIGN PATENT DOCUMENTS

| EP | 0 531 219 A1 | 9/1992 |
| JP | 6-87742 A | 3/1994 |
| WO | WO 01/21607 | * 3/2001 |
| WO | WO 01/74813 A2 | 10/2001 |

OTHER PUBLICATIONS

International Search Report dated May 11, 2004.
Ronald Mierzwa, et al., "Verongamine, a Novel Bromotyrosine-Derived Histamine $H_3$-Antagonist From the Marine Sponge Verongula Gigantea", Journal of Natural Products, vol. 57, No. 1, Jan. 1994, pp. 175-177.
Judith Polonsky, et al., "Isolation and Structure (X-Ray Analysis) of Marcfortine A, a New Alkaloid from *Penicillium roqueforti*", J.C.S. Chem. Comm., 1980, 2 pages.

* cited by examiner

*Primary Examiner*—Charanjit S Aulakh
(74) *Attorney, Agent, or Firm*—Sughrue Mion, PLLC

(57) ABSTRACT

This invention provides novel PF1270A substance, PF1270B substance and PF1270C substance represented by the following formula (1) or pharmaceutically acceptable salts thereof, a method for producing the same and a pharmaceutical composition which comprises at least one of the same as the active ingredient. Since a group of the PF1270 substances of the invention show high affinity for histamine $H_3$ receptor, they are expected as novel histamine $H_3$ receptor ligands useful as medicaments.

(I)

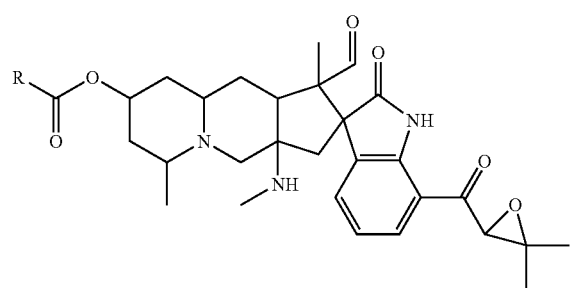

6 Claims, No Drawings

US 7,501,431 B2

PHYSIOLOGICALLY ACTIVE SUBSTANCES PF1270A, B AND C SUBSTANCES

TECHNICAL FIELD

This invention relates to novel physiologically active substances PF1270A, B and C substances or salts thereof, production methods thereof and pharmaceutical compositions containing the same as an active ingredient. The compounds of the present invention show high binding affinity for histamine $H_3$ receptor. Accordingly, the compounds of the present invention are useful for the treatment or prevention of diseases related to histamine $H_3$ receptor.

BACKGROUND OF THE INVENTION

Histamine is one of the biological amines broadly distributed in biological tissues. Its pharmacological activities are transferred into cells via histamine receptors existing on the cell surface. Histamine $H_1$, $H_2$ and $H_3$ receptors have so far been known as the histamine receptors [Ash and Schild, *Br. J. Pharmac. Chemother.*, vol. 27, pp. 427-439, 1966, Black et al., *Nature*, vol. 236, pp. 385-390, 1972, Arrang et al., *Nature*, vol. 302, pp. 832-837, 1983]. In addition, finding of $H_4$ receptor has recently been reported [Oda et al., *J. Biol. Chem.*, vol. 275, pp. 36781-36786, 2000], and various studies are still under progress on histamine receptors and ligands thereof.

Among them, it has been revealed that histamine $H_3$ receptor regulates synthesis and release of histamine as an autoreceptor [Arrag et al., *Neuroscience*, vol. 15, pp. 533-561, 1985, Arrag et al., *Neuroscience*, vol. 23, pp. 149-157, 1978], and (R)-alpha-methylhistamine is known as a selective agonist, and thioperamide as an antagonist [Arrang et al., *Nature*, vol. 327, pp. 117-123, 1987]. In addition, it has been reported that histamine $H_3$ receptor has a function as a hetero-receptor which controls release of serotonin, noradrenalin, dopamine and the like various neurotransmitters in the brain [Schlicker et al., *Naunyn-Schmiedeberg's Arch. Pharmacol.*, vol. 337, pp. 588-590, 1988, Schlicker et al., *Naunyn-Schmiedeberg's Arch. Pharmacol.*, vol. 340, pp. 633-638, 1989, Schlicker et al., *J. Neural Transm.*, vol. 93, pp. 1-10, 1993]. In addition, it has been reported that histamine $H_3$ receptor is also concerned in the release of norepinephrine and calcitonin gene-related peptide (CGRP) at the time of ischemia of heart muscle [Imamura et al., *Circ. Res.*, vol. 78, pp. 475-481, 1996, Imamura et al., *Circ. Res.*, vol. 78, pp. 863-869, 1996].

Several compounds have so far been found as histamine $H_3$ receptor ligands, and their application to medicaments have been attempted. For example, in the case of GT-2331 as a histamine $H_3$ receptor antagonist, clinical test is in progress now on attention-deficit hyperactivity disorder (ADHD) as the indication disease [Tozer and Kalindjian, *Exp. Opin. Ther. Patents*, vol. 10, pp. 1045-1055, 2000]. Also, a histamine $H_3$ receptor agonist BP-2.94 is now under clinical test on asthma as the indication disease [Fozard, *Curr. Opin. Investig. Drugs*, vol. 1, pp. 86-89, 2000].

In addition to these, EP0531219A1 describes that histamine $H_3$ receptor agonists can be expected to be applicable as an anti-migraine tranquilizer, sleep-inducer, an hypnotic, sedative, anxiolytic, anti-asthmatic and anti-inflammatory agent, notably for the bronchi, the skin or eyes, or as an anti-gastric ulcer agent, and the like. In addition, International Publication WO 2001/6865, International Publication WO 99/05115, International Publication WO 99/05141, International Publication WO 99/05141 and the like describe that it is possible to use histamine $H_3$ receptor ligands as therapeutic agents for obesity, type II diabetes, epilepsy, sleep disorders, depression, Alzheimer disease and the like.

As an example of a histamine $H_3$ receptor ligand screened from natural resources, verongamine isolated from a sponge has been reported [Mierzwa et al., *J. Nat. Prod.*, vol. 57, pp. 175-177, 1994]. Including Verongamine, most of the conventional histamine $H_3$ receptor ligands have imidazole ring, which is present in the structure of the endogenous ligand histamine. However, the PF1270A, B and C substances of the present application are novel histamine $H_3$ receptor ligands which do not have the imidazole ring. Known microbial products structurally related to the compounds of the present invention include Marcfortine A which was reported for the treatment and prevention of parasitic diseases [Polonsky et al., *J. Chem. Soc. Chem. Commun.*, pp. 601-602, 1980, U.S. Pat. No. 4,866,060], and the like. However, the compounds of the present application are novel substances whose structures are different from those of the already known compounds so far reported.

An object of the present invention is to provide novel histamine $H_3$ receptor ligands useful for the treatment or prevention of various diseases in which histamine $H_3$ receptor is concerned.

DISCLOSURE OF THE INVENTION

Based on the aforementioned consideration, the present inventors have screened novel compounds from microbial products for the purpose of finding more effective and safe novel histamine $H_3$ receptor ligands. As a result, it was found that histamine $H_3$ receptor ligands are produced and accumulated in the culture of a strain belonging to the genus *Penicillium* (*Penicillium waksmanii* PF1270) newly isolated from soil and named strain PF1270 by the inventors. Thereafter, we have found that these active substances have a chemical structure represented by the following formula (1), confirmed that they are novel substances, and named these substances as PF1270A substance, PF1270B substance and PF1270C substance. The present invention was completed based on these findings.

That is, the invention provides the following novel physiologically active substances PF1270A substance, PF1270B substance and PF1270C substance or pharmaceutically acceptable salts thereof.

A compound represented by a formula (1)

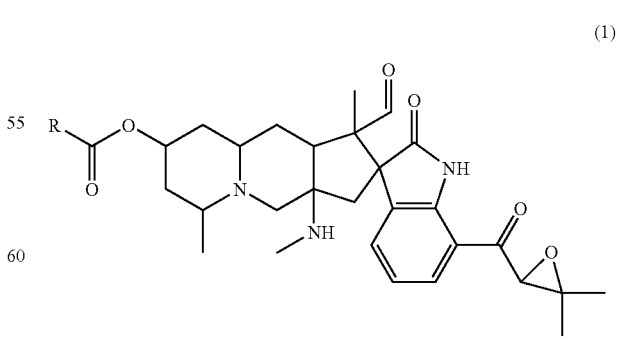

(in the formula, R represents methyl group, ethyl group or propyl group) or a pharmaceutically acceptable salt thereof.

A PF1270A substance represented by a formula (2)

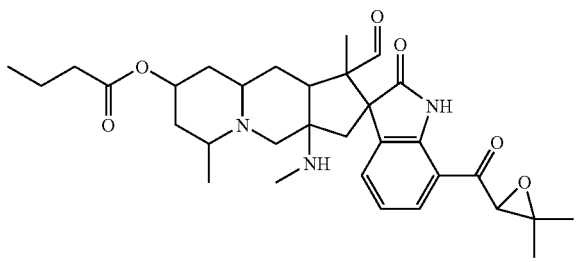

or a pharmaceutically acceptable salt thereof.

A PF1270B substance represented by a formula (3)

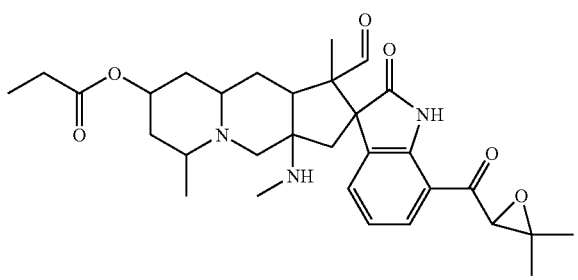

or a pharmaceutically acceptable salt thereof.

A PF1270C substance represented by a formula (4)

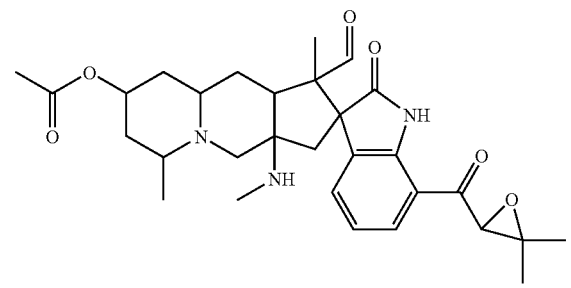

or a pharmaceutically acceptable salt thereof.

Also, the present invention is a method for producing PF1270A, B and C substances, which comprises culturing a strain belonging to the genus *Penicillium* and having the ability to produce PF1270A substance, PF1270B substance and PF1270C substance, and collecting the PF1270A, B and C substances from the culture.

In addition, a pharmaceutical composition which comprises, as the active ingredient, at least one of a strain PF1270 which has the characteristic to produce PF1270A substance, PF1270B substance and PF1270C substance and has been deposited as the deposition number FERM BP-08610 in International Patent Organism Depositary, National Institute of Advanced Industrial Science and Technology, and mutants thereof, and PF1270A, B and C substances and pharmaceutically acceptable salts thereof.

BEST MODE FOR CARRYING OUT THE INVENTION

The first gist of the present invention resides in a novel histamine $H_3$ receptor ligand, PF1270A substance, which is represented by the formula (2) and has the following physicochemical properties.

1. Physicochemical Properties of the PF1270A Substance
   (1) Color and property: yellowish white powder
   (2) Molecular formula: $C_{32}H_{43}N_3O_6$
   (3) Mass spectrum (HRFAB-MS):
       found 566.3224 $(M+H)^+$
       calcd. 566.3230
   (4) Melting point: 173-175° C.
   (5) Specific rotation: $[\alpha]_D^{25}=+75.0°$ (c 1.0, $CH_3CN$)
   (6) Ultraviolet ray absorption spectrum [$\lambda_{max}$ nm ($\epsilon$)]:
       $CH_3CN$ solution
       202 (25200), 228 (18800), 246 (24600), 334 (9030)
       $CH_3CN$-1 N HCl solution (10:1)
       201 (24800), 227 (19000), 245 (24100), 330 (8970)
       $CH_3CN$-1 N NaOH solution (10:1)
       204 (25900), 228 (18500), 246 (24000), 331 (8830)
   (7) Infrared absorption spectrum [$\nu_{max}$ cm$^{-1}$ (KBr)]:
       3384, 2934, 1721, 1674, 1601, 1445, 1381, 1254, 1184, 1090, 1069, 764
   (8) $^1$H-NMR spectrum (400 MHz, $CDCl_3$)
       δ (ppm): 0.98 (3 H, t, J=7.3 Hz), 1.14 (3 H, s), 1.14 (3 H, d, J=6.6 Hz), 1.20 (1 H, m), 1.26 (3 H, s), 1.50 (1 H, br t, J=12.9 Hz), 1.61 (3 H, s), 1.67 (1 H, sext, J=7.3 Hz), 1.67 (1 H, m), 1.85 (1 H, m), 1.85 (1 H, m), 1.98 (1 H, d, J=13.4 Hz), 2.00 (1 H, m), 2.13 (1 H, d, J=13.4 Hz), 2.25 (3 H, s), 2.30 (2 H, td, J=7.3, 3.1 Hz), 2.34 (1 H, d, J=11.2 Hz), 2.49 (1 H, dd, J=13.7, 2.9 Hz), 2.79 (1 H, br t, J=9.8 Hz), 3.01 (1 H, d, J=11.2 Hz), 3.07 (1 H, br t, J=6.3 Hz), 4.05 (1 H, s), 5.10 (1 H, br t, J=2.4 Hz), 7.16 (1 H, t, J=7.6 Hz), 7.76 (1 H, d, J=7.6 Hz), 7.94 (1 H, d, J=7.6 Hz), 9.35 (1 H, s), 9.64 (1 H, br s)
   (9) $^{13}$C-NMR spectrum (100 MHz, $CDCl_3$)
       δ (ppm): 201.9, 194.7, 182.1, 173.1, 143.0, 134.5, 134.2, 127.4, 121.8, 117.2, 68.0, 64.2, 62.7, 61.5 (×2), 58.7, 56.7, 53.9, 50.6, 47.0, 44.8, 37.8, 36.8, 35.5, 30.5, 29.2, 24.3, 18.6, 18.4, 17.9, 13.7, 13.2
   (10) Solubility: soluble in chloroform and methanol, hardly soluble in water.

The second gist of the invention resides in a novel histamine $H_3$ receptor ligand, PF1270B substance, which is represented by the formula (3) and has the following physicochemical properties.

2. Physicochemical Properties of the PF1270B Substance
   (1) Color and property: yellowish white powder
   (2) Molecular formula: $C_{31}H_{41}N_3O_6$
   (3) Mass spectrum (HRFAB-MS):
       found 552.3077 $(M+H)^+$
       calcd. 552.3073
   (4) Melting point: 176-178° C.
   (5) Specific rotation: $[\alpha]_D^{25}=+82.8°$ (c 1.0, $CH_3CN$)
   (6) Ultraviolet ray absorption spectrum [$\lambda_{max}$ nm ($\epsilon$)]:
       $CH_3CN$ solution
       201 (23800), 228 (17200), 246 (22400), 334 (8110)
       $CH_3CN$-1 N HCl solution (10:1)
       201 (23800), 227 (17400), 245 (21800), 331 (8060)
       $CH_3CN$-1 N NaOH solution (10:1)
       205 (26100), 228 (17100), 245 (21800), 331 (8010)
   (7) Infrared absorption spectrum [$\nu_{max}$ cm$^{-1}$ (KBr)]:
       3411, 2942, 1728, 1673, 1603, 1450, 1381, 1255, 1188, 1092, 1069, 762
   (8) $^1$H-NMR spectrum (400 MHz, $CDCl_3$)

δ (ppm): 1.13 (3 H, d, J=6.8 Hz), 1.15 (3 H, s), 1.15 (3 H, t, J=7.6 Hz), 1.21 (1 H, m), 1.25 (3 H, s), 1.50 (1 H, br t, J=13.0 Hz), 1.60 (3 H, s), 1.66 (1 H, m), 1.85 (1 H, m), 1.85 (1 H, m), 1.97 (1 H, d, J=13.4 Hz), 1.99 (1 H, m), 2.13 (1 H, d, J=13.4 Hz), 2.25 (3 H, s), 2.34 (2 H, qd, J=7.3, 2.7 Hz), 2.34 (1 H, d, J=11.2 Hz), 2.49 (1 H, dd, J=13.7, 3.4 Hz), 2.81 (1 H, br t, J=9.3 Hz), 3.00 (1 H, d, J=11.2 Hz), 3.06 (1 H, br t, J=6.4 Hz), 4.05 (1 H, s), 5.08 (1 H, br t, J=2.9 Hz), 7.16 (1 H, t, J=7.8 Hz), 7.76 (1 H, d, J=7.8 Hz), 7.94 (1 H, d, J=7.8 Hz), 9.33 (1 H, s), 9.65 (1 H, br s)

(9) $^{13}$C-NMR spectrum (100 MHz, CDCl$_3$)

δ (ppm): 201.9, 194.7, 182.1, 173.9, 143.0, 134.5, 134.2, 127.4, 121.8, 117.2, 68.2, 64.2, 62.7, 61.5 (×2), 58.7, 56.7, 53.9, 50.5, 47.0, 44.8, 37.8, 35.4, 30.5, 29.2, 28.1, 24.3, 18.6, 17.9, 13.2, 9.1

(10) Solubility: soluble in chloroform and methanol, hardly soluble in water.

The third gist of the invention resides in a novel histamine H$_3$ receptor ligand, PF1270C substance, which is represented by the formula (4) and has the following physicochemical properties.

3. Physicochemical Properties of the PF1270C Substance
(1) Color and property: yellowish white powder
(2) Molecular formula: $C_{30}H_{39}N_3O_6$
(3) Mass spectrum (HRFAB-MS):
  found 538.2917 (M+H)$^+$
  calcd. 538.2917
(4) Melting point: 187-189° C.
(5) Specific rotation: $[\alpha]_D^{25}$=+79.6° (c 1.0, CH$_3$CN)
(6) Ultraviolet ray absorption spectrum [$\lambda_{max}$ nm (ε)]:
  CH$_3$CN solution
   199 (20700), 228 (13300), 247 (17700), 334 (6380)
  CH$_3$CN-1 N HCl solution (10:1)
   199 (21600), 228 (13400), 245 (17200), 331 (6350)
  CH$_3$CN-1 N NaOH solution (10:1)
   203 (24400), 228 (13300), 246 (17300), 331 (6330)
(7) Infrared absorption spectrum [$\nu_{max}$ cm$^{-1}$ (KBr)]:
  33382, 2964, 1732, 1676, 1605, 1453, 1381, 1250, 1190, 1103, 1069, 758
(8) $^1$H-NMR spectrum (400 MHz, CDCl$_3$)

δ (ppm): 1.14 (3 H, d, J=6.8 Hz), 1.14 (3 H, s), 1.21 (1 H, m), 1.26 (3 H, s), 1.50 (1 H, br t, J=12.7 Hz), 1.61 (3 H, s), 1.67 (1 H, m), 1.88 (1 H, m), 1.88 (1 H, m), 1.96 (1 H, d, J=13.4 Hz), 1.98 (1 H, m), 2.07 (3 H, s), 2.13 (1 H, d, J=13.4 Hz), 2.25 (3 H, s), 2.34 (1 H, d, J=11.0 Hz), 2.49 (1 H, dd, J=13.4, 2.9 Hz), 2.82 (1 H, br t, J=9.5 Hz), 3.00 (1 H, d, J=11.0 Hz), 3.06 (1 H, br t, J=6.1 Hz), 4.05 (1 H, s), 5.07 (1 H, s), 7.16 (1 H, t, J=7.6 Hz), 7.76 (1 H, d, J=7.6 Hz), 7.94 (1 H, d, J=7.6 Hz), 9.34 (1 H, s), 9.64 (1 H, br s)

(9) $^{13}$C-NMR spectrum (100 MHz, CDCl$_3$)

δ (ppm): 201.9, 194.7, 182.1, 170.6, 143.0, 134.5, 134.3, 127.4, 121.8, 117.2, 68.4, 64.2, 62.7, 61.5 (×2), 58.7, 56.7, 53.9, 50.5, 47.0, 44.7, 37.8, 35.3, 30.5, 29.2, 24.3, 21.5, 18.6, 17.9, 13.1

(10) Solubility: soluble in chloroform and methanol, hardly soluble in water.

The compounds of the invention can exists as salts, and examples of such salts include salts with hydrochloric acid, sulfuric acid, nitric acid, phosphoric acid and the like inorganic acids or salts with acetic acid, citric acid, benzoic acid, maleic acid and the like organic acids.

The fourth gist of the present invention reside in a method for producing PF1270A, B and C substances, comprising culturing a strain which belongs to the genus *Penicillium* and produces PF1270A substance shown by the aforementioned formula (2), PF1270B substance shown by the aforementioned formula (3) and PF1270C substance shown by the aforementioned formula (4), and collecting the PF1270A, B and C substances are collected from the culture.

As the producer strain of PF1270A, B and C substances, the strain PF1270 newly isolated by the inventors may for example be cited. In this connection, the producer strain of PF1270A, B and C substances is not limited to the specific microorganism described therein, and any strain having the ability to produce PF1270A, B and C substances may be used as the PF1270A, B and C substances producing strain. As suitable examples of the microorganism which may be used, the strain PF1270, or sub-cultured strains, artificial mutants, spontaneous mutants, recombinant strains and the like of such fungal strains. Mycological properties of the strain PF1270 are as follows.

4. Mycological Properties of Strain PF1270
(1) Properties on Respective Media

Growth on Czapek's yeast extract agar medium is good, and a colony of from 18 to 26 mm is formed at 25° C. for 7 days. It consists of grayish green, velvety, flat, thick and dense mycelial layer, and richly forms conidia. The backside becomes dense yellow. Growth on malt extract agar medium is slightly repressive, and a colony of from 17 to 19 mm is formed at 25° C. for 7 days. It consists of grayish green, velvety, flat and mild mycelial layer, and richly forms conidia. The backside becomes dense yellow. It does not grow on all media when cultured at 37° C.

(2) Morphological Properties

Penicillus is monoverticillate or multiverticillate, and phialide is an ampoule shape of 6 to 8×1.5 to 2 μm. The conidium is spherical to sub-spherical shape of 2 to 3 μm, and its surface becomes smooth surface.

Based on the above mycological properties, this fungal strain was identified as *Penicillium waksmanii*. As the reference literature for the identification, The genus *Penicillium* and its teleomorphic states *Eupenicillium* and *Talaromyces* (edited by I. Pitt, Academic Press, London, 1979) was used. In this connection, this fungal strain has been deposited as FERM BP-08610 in International Patent Organism Depositary, National Institute of Advanced Industrial Science and Technology as follow.

(1) Depository: International Patent Organism Depositary, National Institute of Advanced Industrial Science and Technology Address: Central 6, 1-1-1 Higashi, Tsukuba, Ibaraki, Japan (postal code 305-8566)

(2) Deposition date: Original deposition date: Feb. 24, 2003

Date requested for transfer: Feb. 3, 2004 (transfer from the FERM P-19225 deposited on Feb. 24, 2002)

(3) Deposition number: FERM BP-08610

5. Culturing Method of PF1270A, B and C Substances Producing Strain

According to the method of the invention, the strain PF1270 belonging to the genus *Penicillium* is cultured using a medium containing nutrients which can be used by general microorganisms.

Regarding the nutrient sources, conventionally known materials which are generally used for the culturing of fungi can be used. For example, as the carbon source, glucose, sucrose, starch syrup, dextrin, starch, glycerol, molasses, animal or plant oil and the like can be used. Also, soybean flour, soybean cake, wheat germ, corn steep liquor, cotton seed cake, meat extract, peptone, yeast extract, ammonium sulfate, sodium nitrate, urea and the like can be used as the nitrogen source. In addition to these materials, it is effective to add sodium, potassium, calcium, magnesium, cobalt, chlorine, phosphoric acid, sulfuric acid and inorganic salts which can form other ions, as occasion demands. Also, organic and inorganic substances capable of assisting growth of the strain and of accelerating production of the PF1270A, B and C substances can be appropriately added.

As the culturing method, a culturing method under an aerobic condition, particularly a static culturing, is most suitable. The temperature suitable for the culturing is from 20 to 30° C., but the culturing is carried out at around 25° C. in most cases. Regarding production of the PF1270A, B and C substances, their accumulation reaches the maximum generally after 2 to 20 days by any one of the static culture, shaking culture and jar fermentor (jar) culture, though it varies depending on the medium and culture conditions. When accumulation of the PF1270A, B and C substances in the culture reached their maximum, the culturing is stopped, and the substances of interest are isolated and purified from the culture.

6. Purification Method of PF1270A, B and C Substances

Since the PF1270A, B and C substances obtained by the invention have the aforementioned physicochemical properties, it is possible to purify them from the culture in accordance with the properties. For example, after extracting the PF1270A, B and C substances from the culture using an organic solvent, it is possible to purify them using an adsorption desorption method which uses an adsorbent, a molecular partition method which uses a gel filtration agent, a recrystallization method from an appropriate solvent, or the like.

For example, a culture containing the active components is treated with an adsorbent DIAION HP20 (manufactured by Mitsubishi Chemical) to effect adsorption of the active components. Subsequently, they are eluted with acetone, water or the like solvent, the solvent is evaporated by concentrating the eluate under a reduced pressure, and the residue is made into an aqueous solution. This aqueous solution is extracted with ethyl acetate, the extract is concentrated under a reduced pressure, the residue is dissolved in a small amount of chloroform, methanol or the like organic solvent and applied to a silica gel column, and a column chromatography is carried out using a chloroform/methanol, hexane/ethyl acetate or the like solvent system. Thereafter, the PF1270A, B and C substances can be isolated and purified by carrying out a fractional HPLC using an acetonitrile/phosphoric acid or the like solvent system, and further carrying out a fractional thin layer chromatography using a chloroform/methanol, hexane/ethyl acetate or the like solvent system. In addition, it is possible to carry out recrystallization using hexane, chloroform, ethyl acetate, acetone, methanol, water or the like solvent alone or an appropriate combination thereof.

The PF1270A, B and C substances are histamine $H_3$ receptor ligands as described later in Test Example, and it is useful to administer them as a medicament to animals including human. Since the PF1270A, B and C substances as the compounds of the invention have high binding affinity for the histamine $H_3$ receptor, they are useful as therapeutic agents or preventive agents such as anti-dementia agent, an anti-ADHD (attention-deficit hyperactivity disorder) agent, an anti-epilepsy agent, an anxiolytic drug, an anti-schizophrenia agent, an antidepressant, an sleeplessness improving agent, an analgesic, a migraine treating agent, an anti-asthma agent, an anti-inflammatory agent, an anti-ulcerative agent, an anti-obesity agent, a myocardial infarction prognosis improving agent, a somnifacient, an anesthetic agent, a type II diabetes treating agent and the like.

When the PF1270A, B and C substances of the invention are administered as a medicament, they are made into pharmaceutical preparations in accordance with the usual way in response to the respective administration forms or using forms.

As the preparations for oral administration, tablets, pills, granules, capsules, powders, solutions, suspensions, syrups, sublingual preparations and the like can be exemplified. Also, as the preparations for parenteral administration, injections, percutaneous absorption preparations, inhalations, suppositories and the like can be exemplified. In preparing pharmaceutical preparations, surfactants, fillers, stabilizing agents, moistening agents, disintegrating agents, solubilization assisting agents, tonicity agents, buffer agents, coloring agents, flavors and the like additive agents for medicaments are optionally used.

The dose as a medicament varies depending on the age and body weight of each patient, kind and degree of each disease and route of administration, but it is administered within the range of from 0.02 to 200 mg/kg per day per adult when orally administered to human, or from 0.01 to 100 mg/kg per the same in the case of intravenous administration.

EXAMPLES

Though inventive and test examples of the invention are shown in the following, the invention is not limited thereto, and all of the variation and modification means not shown herein are included therein.

Example 1

1. Culturing of PF1270A, B and C Substances Producing Strain

A medium consisting of a composition of 2.0% starch, 1.0% glucose, 0.5% polypeptone, 0.6% wheat germ, 0.3% yeast extract, 0.2% soybean cake and 0.2% calcium carbonate (pH 7.0 before sterilization) was used as the seed culture medium. Also, a solid medium prepared by adding 2.5% of soybean cake to sufficiently water-absorbed rice was used as the production medium.

A 100 ml capacity conical flask into which 20 ml of the aforementioned seed culture medium had been dispensed was sterilized at 120° C. for 15 minutes, and one loopful of slant agar culture of the strain PF1270 (FERM P-19225) was inoculated therein and then cultured at 25 PF1270 for 3 days on a shaker. Next, 500 ml capacity conical flasks into which the production medium had been dispensed in 100 g portions were sterilized at 120° C. for 15 minutes, and the aforementioned seed culture medium was inoculated in 3 ml portions therein, thoroughly stirred and then statically cultured at 25° C. for 14 days. A 10 kg portion of the thus obtained culture was extracted with 20 liters of 67% acetone water, and the extract was concentrated under a reduced pressure to evaporate acetone.

2. Purification of PF1270A, B and C Substances

A 6.5 liter portion of the thus obtained aqueous solution was adjusted to pH 7 with 1 N sodium hydroxide solution and then passed through a column (inner diameter 60 mm×200 mm) of an adsorbent DIAION HP20 (manufactured by Mitsubishi Chemical) to effect adsorption of the active components, and the column was washed with 3 liters of water and 3 liters of 50% acetone water, and then the active components were eluted with 3 liters of acetone. A 3 liter portion of water was added thereto, acetone was evaporated by concentration under a reduced pressure, and the resulting aqueous solution was adjusted to pH 9 with 1 N sodium hydroxide solution and then extracted with 3 liter of ethyl acetate. By concentrating the ethyl acetate layer under a reduced pressure, 3.7 g of a crude extract was obtained. The thus obtained crude extract was dissolved in 50 ml of methanol, 18 g of silica gel (Wako Gel C-300, manufactured by Wako Pure Chemical Industries) was added thereto, and then the crude extract was uniformly adsorbed to silica gel by evaporating methanol under a reduced pressure. This was overlaid on 37 g of silica gel (Wako Gel C-300, manufactured by Wako Pure Chemical Industries) on a glass filter and eluted with hexane/ethyl acetate solution (500 ml for each of 10, 50, 70 and 100% ethyl acetate concentrations), and the fractions containing the active components were combined and concentrated under a reduced pressure to obtain 1.2 g of the residue containing PF1270A, B and C substances.

The thus obtained residue was dissolved in 20 ml of methanol, 6.0 g of silica gel (Wako Gel C-300, manufactured by Wako Pure Chemical Industries) was added thereto, and then the crude extract was uniformly adsorbed to the silica gel by evaporating methanol under a reduced pressure. This was overlaid on 12 g of silica gel (Wako Gel C-300, manufactured by Wako Pure Chemical Industries) on a glass filter and eluted with hexane/ethyl acetate solution (300 ml for each of 10, 20, 30, 40, 50, 60 and 70% ethyl acetate concentrations), and the fractions containing the active components were combined and concentrated under a reduced pressure to obtain 1.0 g of the residue containing PF1270A, B and C substances.

The thus obtained residue was applied to a silica gel column (Wako Gel C-300, inner diameter 40 mm×160 mm, manufactured by Wako Pure Chemical Industries) filled with a solution of chloroform/methanol=50/1 and eluted with chloroform/methanol=50/1, the fractions containing the active components were combined and concentrated under a reduced pressure, and a small amount of methanol was added thereto. In that case, 154.0 mg of methanol-soluble fraction containing PF1270A substance and 128.0 mg of precipitate containing PF1270A, B and C substances were obtained.

Using the methanol-soluble fraction containing PF1270A substance, separation thin layer chromatography (Kieselgur 60, 0.5 mm, manufactured by Merck) was carried out using a hexane/ethyl acetate (1:10) solution as the developing solvent to obtain 72.3 mg of PF1270A substance as a yellowish white powder.

The precipitate containing PF1270A, B and C substances was dissolved in a small amount of acetonitrile, injected into an HPLC (column: Inertsil ODS-2, inner diameter 20 mm×250 mm, manufactured by G L Science) filled with a solution of acetonitrile/0.005% phosphoric acid=22/78 and eluted with the solution of acetonitrile/0.005% phosphoric acid=22/78. The fractions containing the active components were combined, acetonitrile was evaporated under a reduced pressure, and the residue was adjusted to pH 9 with 1 N sodium hydroxide solution and then extracted with ethyl acetate and concentrated under a reduced pressure to obtain 70.2 mg of PF1270A substance as a yellowish white powder, 22.1 mg of a residue containing PF1270B substance and 10.6 mg of a residue containing PF1270C substance.

Using the residue containing PF1270B substance, separation thin layer chromatography (Kieselgur 60, 0.5 mm, manufactured by Merck) was carried out using a hexane/ethyl acetate (1:5) solution as the developing solvent to obtain 17.0 mg of PF1270B substance as a yellowish white powder.

Using the residue containing PF1270C substance, separation thin layer chromatography (Kieselgur 60, 0.5 mm, manufactured by Merck) was carried out using a hexane/ethyl acetate (1:5) solution as the developing solvent to obtain 6.0 mg of PF1270C substance as a yellowish white powder.

The PF1270A, B and C substances obtained by the invention have affinity for histamine $H_3$ receptor. Affinity of the PF1270A, B and C substances for histamine $H_3$ receptor was examined by a binding inhibition test of a histamine $H_3$ receptor ligand, $N^\alpha$-methylhistamine.

Test Example $N^\alpha$-methylhistamine Binding Inhibition Activity

Rat fore-brain was homogenized in 10 volumes of 0.32 M sucrose solution using a Teflon-glass homogenizer, and the thus obtained homogenate was centrifuged at 1000×g for 10 minutes. The supernatant was centrifuged at 39000×g for 20 minutes to obtain the precipitate. This precipitate was washed with an assay buffer (50 mM Tris (pH 7.4), 5 mM EDTA) by centrifugation. This operation was further carried out twice, and the finally obtained membrane fraction was used as the histamine $H_3$ receptor membrane fraction.

The binding inhibition test was carried out using the thus obtained membrane fraction and a radioactive ligand [$^3$H]$N^\alpha$-methylhistamine (manufactured by Perkin-Elmer Life Science). In the presence of PF1270A, B or C substance, the membrane fraction (55 µg as protein) and 1 nM in final concentration of [$^3$H]$N^\alpha$-methylhistamine were added to 150 µl of the assay buffer and incubated at room temperature for 60 minutes. This was filtered using a unifilter GF/B filter (manufactured by Perkin-Elmer) coated with 0.3% polyethyleneimine and washed three times with 200 µl of the assay buffer. After drying at 50° C. for 1 hour, 30 µl of Microscinti-20 (manufactured by Perkin-Elmer) was added thereto as the scintillator, and the radioactivity was counted using Top Count (manufactured by Perkin-Elmer). The nonspecific binding was determined by adding a large excess of thioperamide (10 µM in final concentration). The binding inhibition ratio of $N^\alpha$-methylhistamine in the presence of PF1270A, B or C substance was calculated based on the following formula.

$$\text{Inhibition ratio (\%)} = \left(1 - \frac{\text{Total binding in the presence of test compound} - \text{Nonspecific binding}}{\text{Total binding in the absence of test compound} - \text{Nonspecific binding}}\right) \times 100$$

The $N^\alpha$-methylhistamine binding inhibition ratio of PF1270A, B and C substances was measured by the aforementioned method, and the 50% inhibition concentration ($IC_{50}$) was used as the $N^\alpha$-methylhistamine binding inhibition activity, with the results shown in Table 1.

TABLE 1

| $N^\alpha$-methylhistamine binding inhibition activity of PF1270A, B and C substances | |
|---|---|
| Compound name | $IC_{50}$ (µg/ml) |
| PF1270A | 0.047 |
| PF1270B | 0.22 |
| PF1270C | 0.41 |

As shown in Table 1, it was shown that the PF1270A, B and C substances of the invention are histamine $H_3$ receptor ligands having strong affinity for histamine $H_3$ receptor.

While the invention has been describe in detail and with reference to specific embodiments thereof, it will be apparent to one skilled in the art that various changes and modifications can be made therein without departing from the spirit and scope of the invention.

This application is based on a Japanese patent application filed on Mar. 31, 2003 (Japanese Patent Application No. 2003-093595), the entire contents thereof being thereby incorporated by reference.

INDUSTRIAL APPLICABILITY

As shown in Test Example, the PF1270A, B and C substances of the invention have the affinity for histamine $H_3$ receptor, and a medicament which uses them as the active ingredient is useful for the treatment or prevention of various diseases in which histamine $H_3$ receptor is concerned.

The invention claimed is:

1. A compound represented by a formula (1)

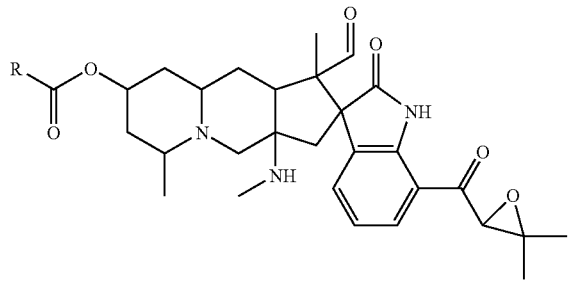

(1)

(in the formula, R represents methyl group, ethyl group or propyl group) or a pharmaceutically acceptable salt thereof.

2. A PF1270A substance represented by a formula (2)

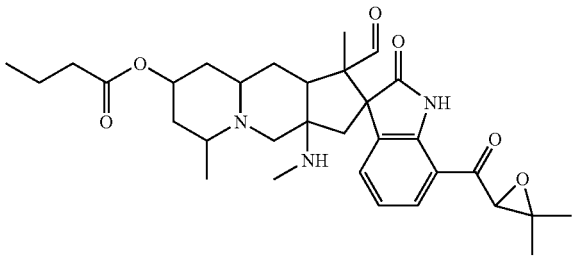

(2)

or a pharmaceutically acceptable salt thereof.

3. A PF1270B substance represented by a formula (3)

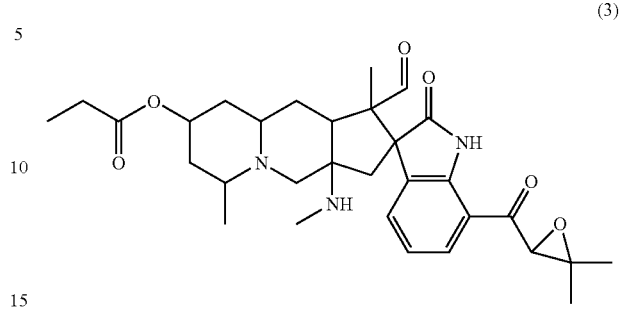

(3)

or a pharmaceutically acceptable salt thereof.

4. A PF1270C substance represented by a formula (4)

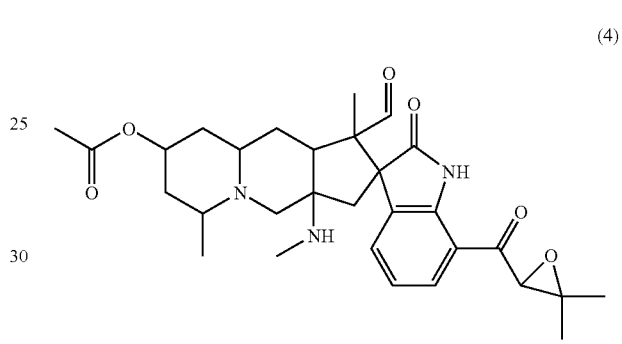

(4)

or a pharmaceutically acceptable salt thereof.

5. A method for producing the compound described in claim 1, comprising culturing *Penicillium waksmanii* and having the ability to produce the compound described in claim 1, and collecting the compound described in claim 1 from the culture.

6. A pharmaceutical composition which comprises, as the active ingredient, the compound described in claim 1 and pharmaceutically acceptable salts thereof.

* * * * *

UNITED STATES PATENT AND TRADEMARK OFFICE
CERTIFICATE OF CORRECTION

PATENT NO. : 7,501,431 B2
APPLICATION NO. : 10/551417
DATED : March 10, 2009
INVENTOR(S) : Nobuaki Kushida et al.

Page 1 of 1

It is certified that error appears in the above-identified patent and that said Letters Patent is hereby corrected as shown below:

Title Page should read
(73) Assignee: ~~Meui~~Meiji Seika Kaisha, Ltd., Tokyo (JP)

Signed and Sealed this

Fifteenth Day of September, 2009

David J. Kappos
*Director of the United States Patent and Trademark Office*